United States Patent [19]

Rogers

[11] Patent Number: 4,466,942
[45] Date of Patent: Aug. 21, 1984

[54] GASEOUS CONTAMINANT DOSIMETER

[75] Inventor: Lockhart B. Rogers, Athens, Ga.

[73] Assignee: E. I. Du Pont de Nemours and Company, Wilmington, Del.

[21] Appl. No.: 425,050

[22] Filed: Sep. 27, 1982

[51] Int. Cl.$^3$ ...................... G01N 31/00; G01N 31/06
[52] U.S. Cl. ........................ 422/61; 422/88; 436/130
[58] Field of Search ............. 422/58, 61, 83, 86, 422/88; 436/128, 129, 130, 165

[56] References Cited

U.S. PATENT DOCUMENTS

| | | | |
|---|---|---|---|
| 4,036,589 | 7/1977 | King | 436/130 |
| 4,201,693 | 5/1980 | Hurt et al. | 436/128 |
| 4,208,371 | 6/1980 | Kring | 422/61 |
| 4,265,635 | 5/1981 | Kring | 23/232 R |
| 4,269,804 | 12/1979 | Kring | 422/86 |
| 4,375,465 | 3/1983 | Drakoff | 424/315 X |
| 4,384,002 | 5/1983 | Stoller | 424/315 |

OTHER PUBLICATIONS

Miksch et al., Analytical Chemistry, vol. 53, 1981, pp. 2118–2123.
Formaldehyde in Air, Physical and Chemical Analysis, Branch, Analytical Method, pp. 125-1 to 125-9, 1/15/74.

Primary Examiner—Arnold Turk
Attorney, Agent, or Firm—Hilmar L. Fricke

[57] ABSTRACT

A personal dosimeter for the collection of formaldehyde is improved by modifying the sodium bisulfite absorbant medium with sodium bicarbonate.

6 Claims, No Drawings

GASEOUS CONTAMINANT DOSIMETER

BACKGROUND OF THE INVENTION

1. Field Of The Invention

This invention is related to a personal dosimeter for registering gaseous contaminants in the atmosphere. More particularly, it is related to a dosimeter for detecting formaldehyde wherein a sodium bisulfite absorbant medium is modified with sodium bicarbonate.

2. Description Of The Prior Art

In response to the increasing concern about the health of workers who are exposed to harmful pollutants in the air, it has become necessary to monitor the concentration of the air-borne contaminants. One development for this purpose involved a rather large air pump which would force air to be sampled through a filter, trapping particulate contaminants. This obviously is unavailing for the monitoring of gaseous contaminants and, even for particles, is not accurate for determining the concentration of the particles in the sampled atmosphere.

Personal sampling devices which are worn by individual workers and which passively collect the contaminants have also been used. For example, a device which utilized the molecular diffusion of the gas to be monitored to collect the sample has been described in the American Industrial Hygiene Association Journal, Volume 34, pages 78–81 (1973). This device and others like it, called impinging tubes, are often cumbersome to use since their designs and delicate constructions necessitate that they always be oriented properly to sample accurately the atmosphere and to prevent dislocation of the sampling mechanism within the tube.

The need arose for the development of personal dosimeters that simply but accurately collected gaseous contaminants in proportion to their average atmospheric concentration. Examples of dosimeters designed for colorimetric analysis are disclosed in Kring U.S. Pat. No. 4,208,371 issued June 17, 1980; Kring et al. U.S. Pat. No. 4,235,097 issued Nov. 25, 1980; and Kring U.S. Pat. No. 4,269,804 issued May 26, 1981. The color intensity of the exposed collecting medium in those dosimeters is proportional to the dose-level of gas sampled. The color stability of suitable collecting mediums, however, is affected by several variables including storage life.

A need became apparent for the availability of a more stable absorbant medium, particularly for dosimeters used in the detection of formaldehyde.

SUMMARY OF THE INVENTION

According to the present invention, there is provided a personal dosimeter for collecting a gaseous contaminant in proportion to its average ambient concentration during the collection time where the dosimeter consists essentially of a closed receptacle;

within the receptacle, an absorbant collecting medium of sodium bisulfite and sodium bicarbonate for the gaseous contaminant;

a diffusion device, forming part of the boundary of the receptacle, the device containing a plurality of through-and-through channels adapted for the gaseous contaminant to diffuse therethrough from the atmosphere to the interior of the receptacle, the channels each having a length-to-diameter ratio of at least 3 and the said channels providing the only communication between the atmosphere and the interior of the receptacle; and a porous, hydrophobic, inert film covering the interior openings of the channels.

The dosimeter of the invention may optionally contain a blister separately sealed and containing a blank of the same sodium bisulfite and sodium bicarbonate medium and also may optionally contain at least one compartment separately sealed and adapted to contain a testing reagent.

DETAILED DESCRIPTION OF THE INVENTION

The dosimeters of this invention collect a gaseous formaldehyde contaminant in proportion to its average concentration in the atmosphere during the collection period and provide for the expedient determination of this concentration. This is achieved by passively sampling the gaseous contaminant in ambient air in proportion to its concentration therein by allowing the contaminant to diffuse into an interior portion of the dosimeter where it is maintained, by an absorbant collection medium situated therein, until it is analyzed.

The collecting medium holds the gaseous contaminant or its ions in a form that is more readily analyzable than is the gaseous form. After collection, the collecting medium and, if used, the blank medium are removed from the dosimeter and treated with appropriate reagents to produce color, the intensity of which is dependent upon the amount of gaseous contaminant collected and analysis of the blank medium. The timeaverage ambient concentration can then be determined, as later explained, with a previously-calibrated colorimeter or spectrophotometer. Alternatively, the contaminant can be separated from the collecting medium and its quantity determined, for example, by gas chromatography wherein the results of the gas chromatography analysis have been previously calibrated against known time-average ambient concentrations of the contaminant. The preferred method of determination is colorimetric.

Generally, the collecting medium is a material that absorbs, adsorbs, reacts or otherwise combines with the gaseous contaminant being measured. Regardless of the manner in which the medium interacts, as above, with the contaminant, the quantity or strength of the collecting medium in the dosimeter should be sufficient to interact very nearly completely with the total quantity of gaseous contaminant which is anticipated to be collected. The collecting medium will often be specific to the particular gaseous contaminant being monitored. Examples, meant to be representative but not limiting, include distilled water or a solution of sodium bisulfite to absorb formaldehyde.

Methods for colorimetric analysis, for example, for sulfur dioxide, nitrogen dioxide, ammonia, or formaldehyde, in air, are described in National Institute for Occupational Safety and Health method numbers 160 (publication 121, 1975), 108 (publication 136, 1974), 205 (publication 121, 1975) and 125 (publication 136, 1974), respectively. The techniques therein described are readily adaptable with respect to absorbing solutions and color-forming reagents for use in connection with collection by the dosimeter of the present invention.

It has now been found that the addition of sodium bicarbonate to the sodium bisulfite absorbant collecting medium reduces decomposition of the bisulfite, thereby improving stability of the collecting medium solution. It has also been found that the addition of the sodium bicarbonate to the sodium bisulfite medium reduces interference from phenol. Phenol is a serious negative interference in chromotropic acid-sulfuric acid analytical procedures for formaldehyde in solution.

The collecting medium solution of this invention generally consists essentially of 0.001 to 3.0% sodium bisulfite by weight based on weight of aqueous solution modified by 0.001 to 2.0% sodium bicarbonate by weight based on weight of aqueous solution. Preferably 0.01 to 2.5% sodium bisulfite by weight based on weight of aqueous solution is modified with 0.01 to 1.0% sodium bicarbonate by weight based on weight of aqueous solution. Most preferably 0.5 to 2.0% sodium bisulfite is modified by 0.02 to 0.05% sodium bicarbonate. A 1% sodium bisulfite by weight based on weight of aqueous solution is modified by 0.03% sodium bicarbonate by weight based on the weight of aqueous solution may be considered a best mode. Concentrations higher than 3.0% of sodium bisulfite and 2.0% sodium bicarbonate can be used but do not appear to provide further benefits.

The sodium bicarbonate modifier can be added to the sodium bisulfite collecting medium by any means known in the art for combining small premeasured quantities of solutions either before or after the sodium bisulfite solution is placed within a dosimeter pouch or blister.

The following Examples illustrate the invention.

EXAMPLE I

A typical dosimeter badge of the invention is assembled from clean thermoformed ionomer resin film to which a molded diffuser of ionomer resin is heat sealed along with a strip of polymers or copolymers of tetrafluoroethylene and hexafluoropropylene. This subassembly is then transferred to a liquid filling station where 2.4±0.1 milliliters of absorbing solution is added to the absorbing and blank solution cavities. The final step is heat sealing a clean flat sheet of ionomer resin over the solution cavities.

The absorbing solution for the formaldehyde badges is formulated as follows:

Dissolve 1.0 gram of sodium bisulfite ($NaHSO_3$) in 100 ml. of (formaldehyde free) distilled-deionized water. Add 0.033 grams of sodium bicarbonate ($NaHCO_3$) to this solution.

EXAMPLE II

A mixed solution of sodium bisulfite and sodium bicarbonate modifier performs as well in sampling formaldehyde in air as an unmodified bisulfite solution as shown by badge tests in exposure chambers containing known but different amounts formaldehyde ($CH_2O$). The calibration factor was the same within error limits with both solutions.

Badges containing either regular or modified absorbing solution were exposed to known concentrations of formaldehyde in air for various time periods. After exposure badges were analyzed by withdrawing 2.0 milliliters (ml.) of absorbing solution and adding 0.3 ml. of 1% chromotropic acid solution and 3.0 ml. of concentrated sulfuric acid, mixing the contents thoroughly, and heating at 90° C. for 15 minutes in a constant temperature hot water bath. After the solutions have cooled to room temperature, the color intensity is read in a standard spectrophotometer using 40 mm light path length rectangular cuvettes. The exposed color activated solution is compared with a similar amount of color activated (unexposed) badge solution. The absorbance difference is divided by the known formaldehyde exposure dose (ppm.hours) to arrive at the calibration factor.

| Exposure Chamber Test | $CH_2O$ ppm. hrs. | Calibration Factor (Absorbance/ppm. hr. $CH_2O$) | |
|---|---|---|---|
| | | Unmodified | Modified |
| 1 | 18.7 | 0.0405 | 0.0419 |
| 2 | 17.9 | 0.0484 | 0.0513 |
| 3 | 18.7 | 0.0518 | 0.0529 |
| 4 | 18.5 | 0.0478 | 0.0458 |
| 5 | 17.7 | 0.0463 | 0.0469 |

EXAMPLE III

In addition to the fact that the bicarbonate modified bisulfite solution performs as well in absorbing formaldehyde as the unmodified solution, it has several other advantages. The first of the advantages of the unmodified solution is that it is noticeably more stable under refrigerated storage conditions as shown by the data below.

| Exposure Chamber Test | Storage Time (Days) Refrig. | % Loss in 1% Bisulfite Via Titration | |
|---|---|---|---|
| | | Unmodified | Modified |
| 1 | 40 | 6 | 0 |
| 2 | 45 | 27 | 0 |
| 3 | 64 | — | 6 |
| 4 | 76 | 33 | — |
| 5 | 88 | 42 | 6 |
| 6 | 129 | 42 | 6 |

EXAMPLE IV

Second, modified solutions are somewhat more stable at room temperature as shown by the following data.

| Test | Storage Time (Days) Room Temp. | % Loss in 1% Bisulfite Via Titration | |
|---|---|---|---|
| | | Unmodified | Modified |
| 1 | 40 | 34 | — |
| 2 | 64 | — | 2.8 |
| 3 | 76 | 49 | — |
| 4 | 88 | 58 | 58 |
| 5 | 129 | 71 | 58 |

The unmodified or regular formaldehyde badge absorbing solution 34% of the bisulfite in solution had decomposed in 40 days at room temperature whereas 2.8% was lost from the modified solution after 64 days. The solution seemed to level off at 58% loss up to 129 days storage whereas the regular solution had lost 71% of the bisulfite. This is how we obtained the stability data.

In Example III and Example IV, solutions of both 1% sodium bisulfite and 1% sodium bisulfite containing 0.03% sodium bicarbonate were stored in clean glass containers under room temperature and refrigerated conditions. After various storage times a 1.0 ml. of each solution is withdrawn from the container and added to 25 ml. of 0.01 normal iodine solution. The unreacted iodine is titrated with 0.01 normal standardized sodium thiosulfate solution using starch solution indicator. The amount of iodine loss is a direct measure of the bisulfite content of the stored absorbing solutions. That is, a standard oxidation-reduction titration method.

EXAMPLE V

Thirdly, absorbance readings for blank solutions are lower when modified with sodium bicarbonate than unmodified solutions as shown by the data below. All values are duplicate reading averages. The differences in absorbance readings are statistically significant.

| Absorbance vs. Distilled Water (40 mm Path) Color Activated By Chromotropic Acid-Sulfuric Acid Procedure | | |
|---|---|---|
| Test | Unmodified | Modified |
| 1 | 0.034 | 0.022 |
| 2 | 0.044 | 0.033 |
| 3 | 0.008 | 0.006 |
| 4 | 0.045 | 0.025 |
| 5 | 0.038 | 0.033 |
| 6 | 0.059 | 0.045 |

The data tabulated in this example were obtained from the color activated blank badges which were used to read out color activated exposed badges as described in Example II. Blank badge solutions after color activation are read out in a 40 mm path cuvette against distilled water in a second 40 mm cuvette. This data is routinely collected after every badge exposure test.

EXAMPLE VI

Finally, the modified bisulfite absorbing solution is affected less by other airborne contaminants present with formaldehyde. The standard NIOSH impinger test P&CAM 125 which specifies water as the absorbing solution lists the following effects of the airborne contaminants. "Ethanol and higher molecular weight alcohols and olefinic compounds in mixtures with formaldehyde are negative interferences." These result in lower color levels for the same amount of formaldehyde. "Phenols result in a 10–20% negative interference (color reduction) when present in an 8:1 excess over formaldehyde. Aromatic hydrocarbons also constitute a negative interference."

When 1% sodium bisulfite is used as the absorbing solution in a passive dosimeter only phenol which has an affinity for the solution is a negative interference as shown in the table below, test 1–4.

| Test | Compound Tested | Dose ppm. hrs. | Percent Change in Color After 20 ppm. hrs. Formaldehyde Sample Dose-Unmodified Abs. Soln. |
|---|---|---|---|
| 1 | Ethanol | 2000 | 0 |
| 2 | n-Butanol | 800 | −2 |
| 3 | Toluene | 1200 | +2 |
| 4 | Phenol | 40 | −16 |
| | | | −Modified Abs. Soln |
| 5 | Phenol | 40 | −4 |

Changes of 0–4% are not statistically significant. The fact that sodium bicarbonate added to sodium bisulfite reduced the interference from phenol from 16 to 4% is a significant effect not expected or anticipated from current literature references.

For example, in the above tests eight badges were first exposed to approximately 20 ppm.hours of formaldehyde. Four of the exposed badges were put in a second chamber and exposed to 500 ppm of ethanol in air for four hours (or 2000 ppm.hours). The same type test was repeated for each of the four contaminants using badges with regular absorbing solution (1% sodium bisulfite). Finally, eight badges containing the modified absorbing solution were exposed to 20 ppm.hours of formaldehyde and four of the exposed badges were exposed to 5 ppm of phenol for eight hours. In each of the five tests the final color of the four control badges was compared with the second four exposed to the interfering contaminant.

In use, a dosimeter of this invention is exposed to the air containing the gaseous contaminant for a period of time for which the average contaminant concentration is sought. When the collecting medium is an absorbing solution, for example, a measured amount of the solution is then withdrawn from the dosimeter by, for example, a hypodermic syringe.

When the analysis is to be made photometrically, the withdrawn absorbing solution is mixed with appropriate color forming reagents which change the color of the absorbing solution. The intensity of color so formed is dependent upon the amount of gaseous contaminant collected. Although it is often desirable to have a self-contained dosimeter, as shown in U.S. Pat. No. 4,208,371, in which the reagents are contained in the dosimeter and no withdrawal of material is necessary, this is sometimes impractical. An example of this is where the reagents are highly acidic, as in the colorproduction for formaldehyde where the reagents are chromotropic acid concentrated sulfuric acid. In such cases, it is difficult to package the reagents in a stable and safe form, and the simple dosimeter of the present invention is well suited for these applications.

The dosimeter of this invention can be calibrated to give a direct relationship between colorimetric or spectrophotometric readings and average ambient concentration of the gaseous contaminant. This can be accomplished by following a calibration procedure similar to that described in U.S. Pat. No. 4,208,371. In such a procedure, several dosimeters are exposed over a given period of time to various known concentrations of contaminant for which the calibration factor is sought. The dosimeters contain the same kinds and amounts of collecting medium. Spectrophotometric readings, for example, are determined for at least two dosimeters at each of several known concentrations, and a straight line is plotted, the slope of which is obtained by using a least-squares analysis, through the data points is the calibration factor in units of absorbance per ppm.hour dose level.

A dosimeter useful in this invention may optionally include a blister separately sealed and containing a blank of the absorbant collecting medium. The blank absorbant medium contained in the added blister is the same absorbing material as present in the diffuser containing absorbing blister. Both media are present in measured amounts. The blank does not increase in absorbance after the dosimeter is exposed to a gaseous contaminant. When the collecting medium is analyzed, the blank absorbant medium from the added, separately sealed blister is used as a standard which has been exposed to the same environmental conditions, particularly shelf-life, as the collecting absorbant medium.

A dosimeter useful in this invention may also optionally contain at least one compartment separately sealed and adapted to contain a testing reagent, the seals of each compartment being individually breakable such that the reagents can be separately released into the reaction chamber as shown in U.S. Pat. No. 4,269,804 issued May 26, 1981 to Kring.

The dosimeters are examples of preferred embodiments of the present invention but the invention is not limited thereto. The diffusion device, for example, can be in the shape of a plug sealed into the face of two sheets. Similarly, the receptacle of the dosimeter need not be pouch-like as hereinbefore referenced, but for example, could be in the form of a rigid cuvette.

What is claimed is:

1. A personal dosimeter for collecting a gaseous contaminant in proportion to its average ambient concentration during the collection time, the dosimeter consisting essentially of
   a closed receptacle;
   within the receptacle, an absorbant collecting medium for the gaseous contaminant of 0.001 to 3.0% sodium bisulfite by weight based on weight of aqueous solution and 0.001 to 2.0% sodium bicarbonate by weight based on weight of aqueous solution;
   a diffusion device, forming part of the boundary of said receptacle, the device containing a plurality of through-and-through channels adapted for the gaseous contaminant to diffuse therethrough from the atmosphere to the interior of the receptacle, said channels each having a length-to-diameter ratio of at least 3 and said channels providing the only communication between the atmosphere and the interior of the receptacle; and
   a porous, hydrophobic, inert film covering the interior openings of said channels.

2. The dosimeter of claim 1 in which the collecting medium is 0.01 to 2.5% sodium bisulfite and 0.01 to 1.0% sodium bicarbonate.

3. The dosimeter of claim 1 in which the collecting medium is 0.5 to 2.0% sodium bisulfite and 0.02 to 0.05% sodium bicarbonate.

4. A personal dosimeter for collecting a gaseous contaminant in proportion to its average ambient concentration during the collection time, the dosimeter consisting essentially of
   a closed receptacle;
   within the receptacle, an absorbant collecting medium for the gaseous contaminant of 0.001 to 3% sodium bisulfite by weight based on weight of aqueous solution and 0.001 to 2.0% sodium bicarbonate by weight based on weight of aqueous solution;
   a blister separately sealed and containing a blank absorbant medium;
   a diffusion device, forming a part of the boundary of said receptacle, the device containing a plurality of through-and-through channels adapted for the gaseous contaminant to diffuse therethrough from the atmosphere to the interior of the receptacle, said channels each having a length-to-diameter ratio of at least 3 and said channels providing the only communication between the atmosphere and the interior of the receptacle; and
   a porous, hydrophobic, inert film covering the interior openings of said channels.

5. The dosimeter of claim 4 in which the collecting medium is 0.01 to 2.5% sodium bisulfite and 0.01 to 1.0% sodium bicarbonate.

6. The dosimeter of claim 4 in which the collecting medium is 0.5 to 2.0% sodium bisulfite and 0.02 to 0.05% sodium bicarbonate.

* * * * *